US008761864B2

(12) United States Patent
Sabol et al.

(10) Patent No.: US 8,761,864 B2
(45) Date of Patent: Jun. 24, 2014

(54) METHODS AND APPARATUS FOR GATED ACQUISITIONS IN DIGITAL RADIOGRAPHY

(75) Inventors: John Michael Sabol, Sussex, WI (US); Kadri Nizar Jabri, Waukesha, WI (US); Renuka Uppaluri, Pewaukee, WI (US); Gopal B. Avinash, Mcnomonee Falls, WI (US)

(73) Assignee: General Electric Company, Schenectady, NY (US)

( * ) Notice: Subject to any disclaimer, the term of this patent is extended or adjusted under 35 U.S.C. 154(b) by 943 days.

(21) Appl. No.: 11/521,192

(22) Filed: Sep. 14, 2006

(65) Prior Publication Data
US 2008/0123812 A1 May 29, 2008

(51) Int. Cl.
*A61B 6/03* (2006.01)
*A61B 6/00* (2006.01)
*A61B 6/02* (2006.01)
*H05G 1/38* (2006.01)
*A61B 5/113* (2006.01)
*A61B 5/00* (2006.01)

(52) U.S. Cl.
CPC ............... *A61B 6/541* (2013.01); *A61B 6/032* (2013.01); *A61B 6/025* (2013.01); *A61B 6/405* (2013.01); *A61B 6/542* (2013.01); *A61B 6/527* (2013.01); *A61B 6/5288* (2013.01); *A61B 6/482* (2013.01); *A61B 6/503* (2013.01); *A61B 6/505* (2013.01); *A61B 5/113* (2013.01); *A61B 5/721* (2013.01); *H05G 1/38* (2013.01)
USPC .................................. 600/428; 378/8; 378/95

(58) Field of Classification Search
USPC ......................................... 600/428; 378/8, 95
See application file for complete search history.

(56) References Cited

U.S. PATENT DOCUMENTS

| 6,643,536 | B2 | 11/2003 | Nicolas et al. |
| 6,661,873 | B2 * | 12/2003 | Jabri et al. ................ 378/98.11 |
| 6,721,386 | B2 | 4/2004 | Bulkes et al. |
| 6,771,999 | B2 | 8/2004 | Salia et al. |
| 7,236,559 | B2 * | 6/2007 | Jha et al. ........................... 378/5 |
| 7,263,214 | B2 * | 8/2007 | Uppaluri et al. .............. 382/128 |
| 7,352,885 | B2 * | 4/2008 | Eberhard et al. ............. 382/131 |
| 7,440,603 | B2 * | 10/2008 | Eberhard et al. ............. 382/131 |
| 8,064,983 | B2 * | 11/2011 | Salla et al. .................... 600/413 |
| 2003/0036693 | A1 | 2/2003 | Avinash et al. |
| 2004/0249314 | A1 | 12/2004 | Saliea et al. |
| 2004/0258286 | A1 | 12/2004 | Salia et al. |
| 2005/0113670 | A1 | 5/2005 | Salia et al. |
| 2005/0113671 | A1 | 5/2005 | Salia et al. |
| 2005/0113672 | A1 | 5/2005 | Salia et al. |

(Continued)

OTHER PUBLICATIONS

Title: A method for selective tissue and bone visualization using dual energy scanned projection radiography; Author Brody et al.; Date: Sep. 22, 1980; pp. 5; Document Info: Med. Phys., 8(3), May/Jun. 1981; 1981 Am. Assoc. Phys. Med.

(Continued)

*Primary Examiner* — Long V. Le
*Assistant Examiner* — Angela M Hoffa
(74) *Attorney, Agent, or Firm* — ZPS Group, SC

(57) ABSTRACT

A method includes automatically determining at least one gating signal based on a physiological signal from a subject being imaged by an imaging system, automatically determining, based upon prior analysis and knowledge of the imaging system's capabilities, a timing of each of a plurality of exposures within a single or multiple cycles of the physiologic signal, and performing the multiple acquisitions.

25 Claims, 6 Drawing Sheets

A schematic illustration of the two different approaches to timing the two exposures in an ECG-gated dual-energy procedure.

(56) References Cited

U.S. PATENT DOCUMENTS

2005/0113674 A1    5/2005   Salia et al.
2005/0113702 A1    5/2005   Salia et al.
2005/0148850 A1*   7/2005   Lahm et al. .................. 600/407

OTHER PUBLICATIONS

Title; The Development and Characterization of a Dual-Energy Subtraction Imaging System for Chest Radiography Based on CsI:Tl Amorphous Silicon Flat-Panel Technology; Author: Sabol et al.; Date: 2001; pp. 10; Document Medical Imaging 2001; Physics of Medical Imaging, Proceedings of SPIE vol. 4320 (2001).

Digital Radiography with Dual-Energy Subtraction: Improved Evaluation of Cardia Calcification; Author: Gilkeson et al.; Date: Nov. 2004; pp. 6; Document: AJR:183.

Title: Dual-Energy Chest Radiography with a Flat-Panel Digital Detector: Revealing Calcified Chest Abnormalities; Author: Fischbach et al.; Date: Dec. 2003; pp. 6; Document: AJR:181.

Title: Dual-Energy Subtraction Chest Radiography: What to Look for beyond Calcified Nodules; Author: Kuhlman et al.; Date 2006; pp. 15; Document: RadioGraphics 2006.

Title: Fast Imaging of a 41cm Amorphous Silicon Flat-panel Detector for Radiographic Applications; Author: Kump; Date: 2001; pp. 7; Document Medical Imaging 2001: Physics of Medical Imaging; Proceedings of SPIE vol. 4320 (2001).

Title: High-Performance Dual-Energy Imaging with a Flat-Panel Detector: Imaging Physics from Blackboard to Benchtop to Bedside; Author: Siewerdsen et al.; Date: 2006; pp. 10; Document: Medical Imaging 2006: Physics of Medical Imaging; Proceedings of SPIE vol. 6142.

Title: Oue-Shot Dual-Energy Subtraction Chest Imaging with Computed Radiography: Clinical Evaluation of Film Images; Author: Ishigaki et al. Date: Jul. 1988; pp. 6; Document: Department of Radiology, Nagoya University School of Medicine.

Title: Performance of a 41X41-cm$^2$ amorphous silicon flat panel x-ray detector for radiographic imaging applications; Author: Granfors et al.; Date: Jun. 2000; pp. 8; Document: Med. Phys. 27 (6); 2000 Am. Assoc. Phys. Med.

Title: Simulated and Experimental Technique Optimization of Dual-Energy Radiography: Abdominal Imaging Application; Author: Sabol et al.; Date: 2006; pp. 12; Document: Medical Imaging 2006: Physics of Medical Imaging, Proceedings of SPIE vol. 6142.

Title: Improvement of Detection in Computed Radiography by New Single-Exposure Dual-Energy Subtraction; Author: Ito et al.; Date: Feb. 1993; pp. 6; Document Journal of Digital Imaging, vol. 6, No. 1.

Title: The Impact of Cardiac Gating on the Detection of Coronary Calcifications in Dual Energy Chest Radiography: A Phantom Study; Author Sabol et al.; Date: 2006; pp. 12; Document: Medical Imaging 2006: Physics of Medical Imaging, Proceedings of SPIE vol. 6142.

\* cited by examiner

Figure 3: Dual-energy bone images of two patients showing minimal (left) and significant (right) motion artifacts.

Figure 4: A schematic illustration of the timing of the two exposures in a gated dual-energy procedure. The Exposure times are shown relative to the cardiac cycle for both the single-cycle and multi-cycle gating modes.

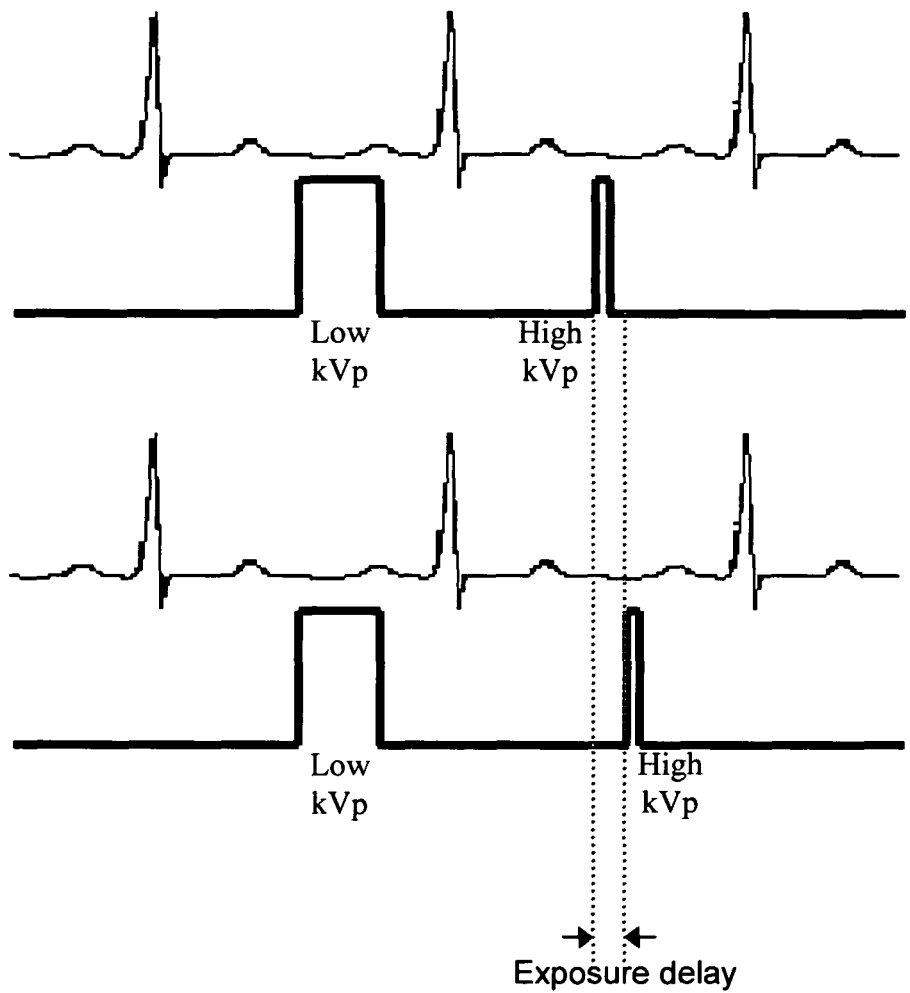
Figure 6: A schematic illustration of the two different approaches to timing the two exposures in an ECG-gated dual-energy procedure.

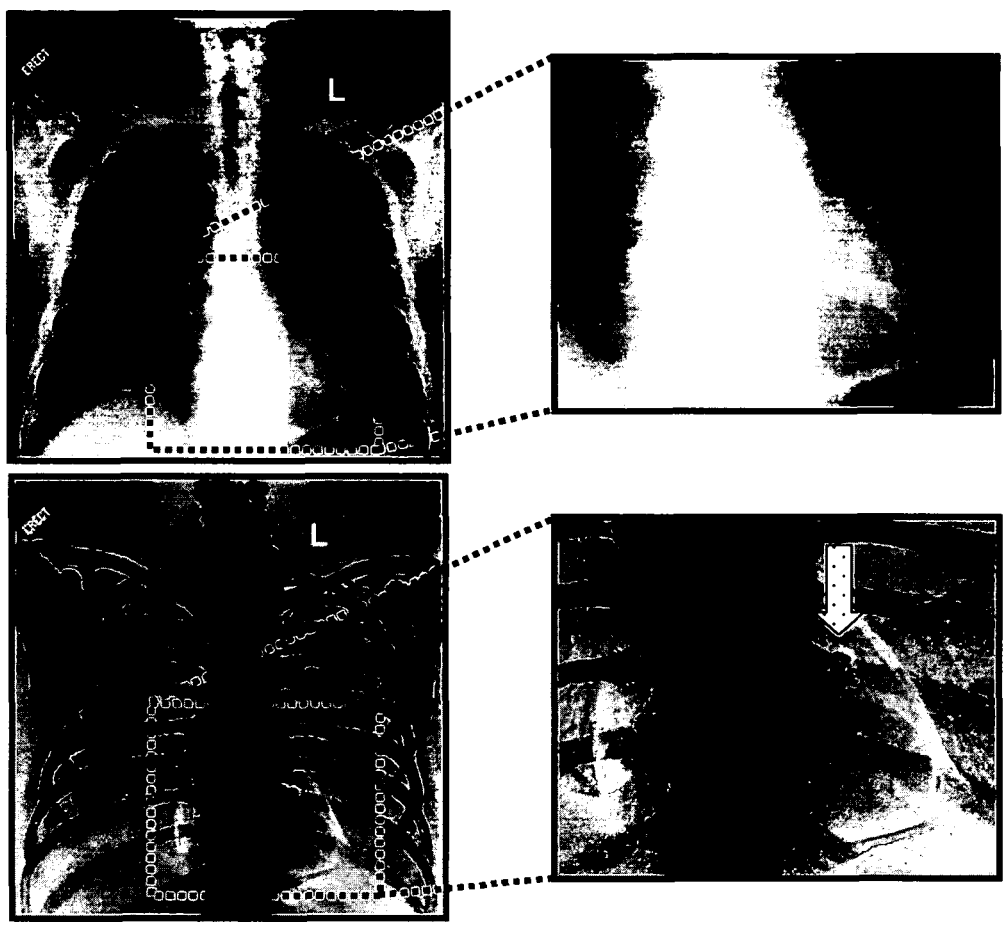
Figure 7: Conventional (single-energy) (upper) and dual-energy bone (lower) images of a patient showing coronary calcifications readily visualized on the bone image.

METHODS AND APPARATUS FOR GATED ACQUISITIONS IN DIGITAL RADIOGRAPHY

BACKGROUND OF THE INVENTION

This invention relates generally to x-ray methods and apparatus, and more particularly to methods and apparatus that provide gating single- and multiple-exposure digital x-ray applications.

X-ray has traditionally been a single exposure modality resulting in a projection image of the anatomy being examined. With the introduction of rapid-readout digital detectors, advanced applications utilizing multiple exposures have been enabled. These advanced applications result in multiple images, which provide additional information to the radiologists to aid in diagnosis.

Dual-energy subtraction imaging has been proposed and investigated by many researchers as a means of reducing the impact of overlying, superimposed anatomic structure on disease detection in chest radiography. Dual-energy is an example of an application where two exposures are acquired in rapid succession, it involves taking two exposures of the patient using different energy x-ray beams. By exploiting the differences in the energy dependence of attenuation between bone and soft tissue, the contrast of the bone can be eliminated producing a soft-tissue only image, or the contrast of the soft tissue can be reduced to produce a bone image. Energy subtraction computed radiography (CR) systems have been developed but are hampered by poor subtraction effectiveness, workflow inconveniences, and the inherent detection inefficiencies of the CR technology. Despite these limitations, CR based dual energy has been shown to increase the detection of lung cancer.

A digital flat-panel imaging system based on a CsI:TI scintillator coupled to an amorphous silicon TFT array has been developed. For radiographic applications, the panel has a size of 41 cm×41 cm, 2048×2048×200 mm pitch. The key enabler for dual-exposure dual-energy imaging is the ability to rapidly read the image data off the commercially available detector. This technology has evolved to the point where these techniques are receiving widespread clinical acceptance and improving the detection of thoracic pathology, and the application of this technique is now being applied to non-thoracic imaging tasks. Improved detection of calcified structures and anecdotal reports of the detection of coronary calcifications have been reported. The clinical significance of these observations is only beginning to be investigated.

Tomosynthesis is another application where several rapid exposures are acquired in rapid succession as the source traverses an angular range relative to the detector. These exposures are used to reconstruct thin image planes through the anatomy being examined. This process removes under- and over-lying structures for a given reconstructed image plane.

With the current dual-energy and tomosynthesis systems, exposures can be acquired with less than a 200 msec interval between acquisitions. Although this interval is relatively short, motion of tissues in this interval can lead to the creation of artifacts in the final subtracted or reconstructed images as shown in one of the Figures for the example of dual-energy imaging. Therefore, we have developed a prototype dual-energy gating system that has been validated on anthropomorphic phantoms.

Currently, with single-exposure or multiple-exposure x-ray imaging, the patient is usually asked to hold their breath. However, there is no mechanism to ensure this, particularly in patients whose health is compromised. Further, since the heart is beating during the procedure, there is no mechanism to ensure that all acquisitions happen at a known point in the cardiac cycle. It is hypothesized that cardiac motion is primarily responsible for observed motion artifacts in thoracic dual-energy imaging, and both cardiac and respiratory motion can cause artifacts during the longer total duration of a tomosynthesis acquisition series.

This is important for two principle reasons:

a) When information from different acquisitions is combined to create an image, if the acquisitions are not exactly aligned, the resulting image will have "mis-registration" artifacts. These artifacts may be aesthetically unpleasing and artifact reduction has always been a goal for all diagnostic imaging (DI) modalities.

b) If quantitative metrics such as size measurements are to be calculated, knowledge of the exact acquisition time with respect to respiratory and cardiac cycles is useful in addition to other system-related information such as distance from source, detector, etc.

Therefore, below are designs and workflows for gating single- and multiple-exposure digital X-ray applications.

BRIEF DESCRIPTION OF THE INVENTION

In one aspect, a method for gating multiple acquisitions is provided. The method includes automatically determining at least one gating signal based on a physiological signal from a subject being imaged by an imaging system, automatically determining, based upon prior analysis and knowledge of the imaging system's capabilities, a timing of each of a plurality of exposures within a single or multiple cycles of the physiologic signal, and performing the multiple acquisitions.

In another aspect, a system includes an x-ray source, an x-ray detector positioned to receive x-rays emitted from the source, and a computer operationally coupled to the source and the detector. The computer is configured to automatically validate both a respiratory cycle of a patient and a cardiac cycle of the patient, and provide an operator with an indication that a gating signal is valid and the time is appropriate to begin multiple gated acquisitions.

In yet another aspect, a system includes an x-ray source, an x-ray detector positioned to receive x-rays emitted from the source, and a computer operationally coupled to the source and the detector. The computer is configured to perform automatic gating and automatic optimization of parameters (AOP).

In still yet another aspect, a system includes an x-ray source, an x-ray detector positioned to receive x-rays emitted from the source, and a computer operationally coupled to the source and the detector. The computer is configured to initiate a first acquisition at a first energy at a first point in a cycle of a cyclically moving object, and initiate a second acquisition at a second energy different from the first energy at a second point in a cycle, wherein the second point is different from the first point.

In yet still another aspect, a system includes an x-ray source, an x-ray detector positioned to receive x-rays emitted from the source, and a computer operationally coupled to the source and the detector. The computer is configured to automatically determine at least one gating signal based on a physiological signal from a subject being imaged by the system; automatically determine, based upon prior analysis and knowledge of the system's capabilities, a timing of each of a plurality of exposures within a single or multiple cycles of the physiologic signal, and perform multiple acquisitions.

BRIEF DESCRIPTION OF THE DRAWINGS

FIG. 6 illustrates two timing approaches to a dual energy acquisition.

FIG. 7 illustrates conventional (single-energy) (upper) and dual-energy bone (lower) images of a patient showing coronary calcifications readily visualized on the bone image.

DETAILED DESCRIPTION OF THE INVENTION

There are herein described methods and apparatus useful for imaging systems such as, for example, but not limited to a digital radiography (DR) System. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention. Although, described in the setting of DR, it is contemplated that the benefits of the invention accrue to all systems with x-ray sources.

Figure 1:
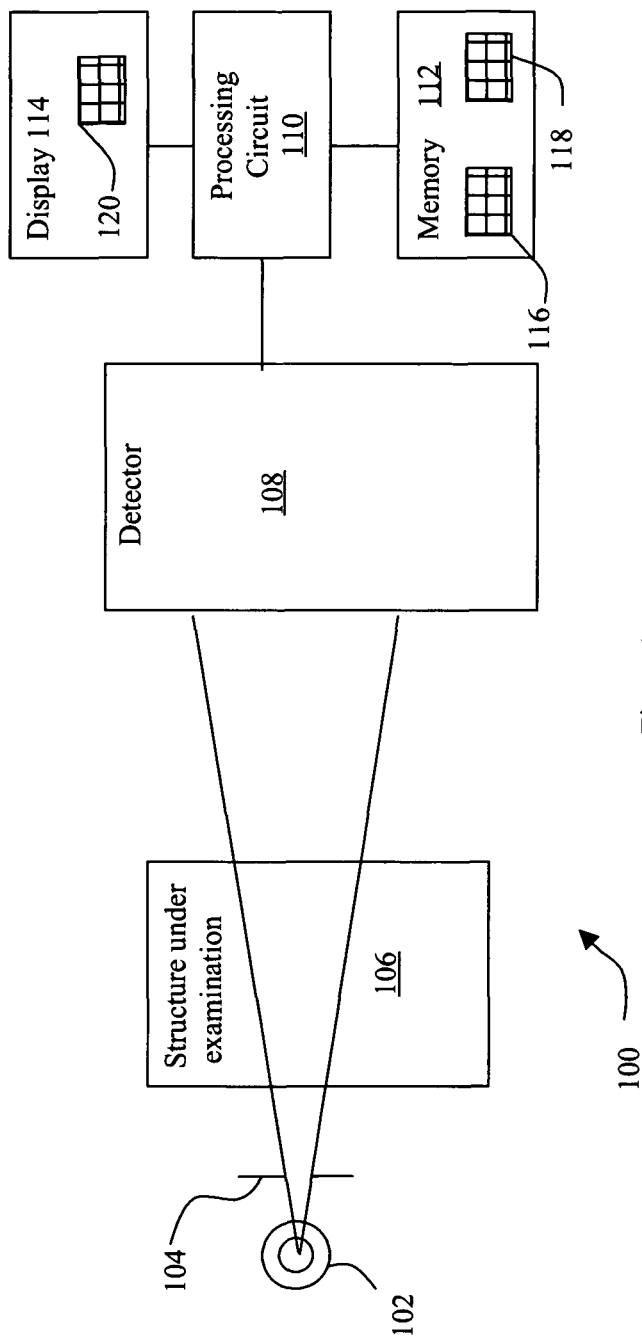
FIG. 1 illustrates an exemplary x-ray imaging system.

FIG. 1 illustrates an exemplary x-ray imaging system 100. The imaging system 100 includes an x-ray source 102 and a collimator 104, which subject the structure under examination 106 to x-ray photons. As examples, the x-ray source 102 may be an x-ray tube, and the structure under examination 106 may be a human patient, test phantom or other inanimate object under test.

The x-ray imaging system 100 also includes a detector 108 coupled to a processing circuit 110. The processing circuit 110 (e.g., a microcontroller, microprocessor, custom ASIC, or the like) is coupled to a memory 112 and a display device 114. The memory 112 (e.g., including one or more of a floppy disk drive, CD-ROM drive, DVD drive, magnetic optical disk (MOD) device, or any other digital device including a network connecting device such as an Ethernet device for reading instructions and/or data from a computer-readable medium, such as a floppy disk, or an other digital source such as a network or the Internet, as well as yet to be developed digital means, and the like) stores a high energy level image 116 (e.g., an image read out from the detector 108 after 110-140 kVp 5 mAs exposure) and a low energy level image 118 (e.g., an image read out after 70 kVp 25 mAs exposure).

Memory 112 may also store a computer program including instructions executed by the processing circuit 110 to implement the functions described herein. Processing circuit 110 provides an image 120 for display on device 114. As described in further detail herein, the image 120 may representative of different structures (e.g., soft-tissue, bone). The detector 108 may be a flat panel solid state image detector, for example, although conventional film images stored in digital form in the memory 112 may also be processed. In one embodiment, processing circuit 110 executes instructions stored in firmware (not shown). Generally, a processor is programmed to execute the processes described below.

Of course, the method is not limited to practice in system 100 and can be utilized in connection with many other types and variations of imaging systems. In one embodiment, processing circuit 110 is a computer that is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits. Although the herein described methods are described in a human patient setting, it is contemplated that the benefits of the invention accrue to non-human imaging systems such as those systems typically employed in small animal research.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also, as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

Figure 2:
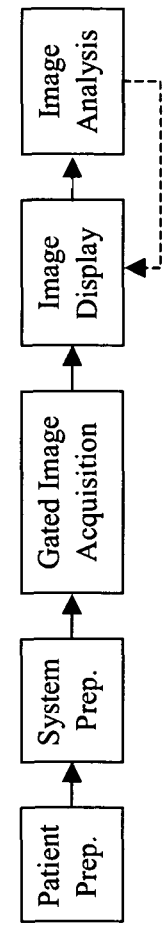
FIG. 2 illustrates stages.
Figure 3:
FIG. 3 illustrates dual-energy bone images of two patients showing minimal (left) and significant (right) motion artifacts.

FIG. 2 illustrates stages as follows:

A. Patient Preparation:

Involves applying any wired and/or wireless contacts required to transduce and transfer the patient's anatomical/physiological signals into inputs to the gating and/or imaging system. These may also include non-standard positioning of the patient with respect to the imaging system as required for a specific gating and/or imaging protocol.

B. System Preparation:

Selection of Protocol:

Comprises automated or operator-initiated selection of appropriate gating and/or imaging protocol. Automated selection may be based on analysis of gating or other patient-derived signals such as heart rate, stability of heart rhythm, and/or respiratory rate, respiratory volume, or stability of respiratory motion.

Validation of Gating Signal:

Comprises verification that the gating signal is valid and ready for use in determining the timing of exposures. For example, determine that the heart rate is within a valid range by detecting five consecutive heart cycles and deriving an average or median heart cycle time. As another example, ensure that the patient is substantially not moving based on a motion sensor response. An optional workflow is for the protocol to be automatically selected after this validation is complete. For example, the heart rate validity may determine if the system acquires the images on a single cardiac or respiratory cycle, or on sequential cycles. The validation phase may include logical combination of multiple gating signals, for example waiting for a valid combination of both cardiac and respiratory gating signals.

Feedback to Operator:

Feedback signals (visual, auditory, etc.) may be provided to the operator to indicate that the preceding two steps are complete. For example, an LED display can indicate that valid heartbeats are detected by the gating system and that the operator can now push the Expose button to start the image acquisition. Other LED display elements may indicate whether or not the patient is breathing. Combinations of visual and auditory signals may be used to indicate when both cardiac and respiratory gating conditions are met.

C. Gated Image Acquisition:

Acquiring one or more images whereby the timing of the exposure(s) is determined by a one- or higher-dimensional gating signal or a derivative thereof. See below for possible gating techniques and gating modes.

D. Image Display:

Display of Acquired Image(s):

Images acquired are displayed for the operator to review. One or more of the images may consequently be transferred to an independent review workstation such as a PACS workstation.

Display of Gating Information:

Information specific to the gating signal and its relation to the imaging technique/timing may be displayed. For example, a small schematic representing where image exposures occurred within the cardiac cycle (ECG) may be added to the image(s) as overlays. Other information related to gating may also be shown as part of image text annotations.

E. Image Analysis:

Quantitative metrics may be automatically derived from the images and/or the gating signals and their relationship. Such metrics may be optionally fed back to the image display. For example, the size of the heart in a dual-energy gated single-beat acquisition may be automatically estimated in each of the two images, and the cardiac ejection fraction derived from the size estimates and the timing of the exposures relative to the cardiac cycle. In addition, a user interface may allow the manual measurement and calculation of specific metrics.

Gating Techniques:

To reduce or eliminate the effects of internal motion, gating techniques, which utilize information about organ motion, may be employed during imaging. Gating techniques that use organ motion information to time the acquisition of imaging data are known as prospective gating techniques. Conversely, those that acquire temporally over sampled image data over several organ motion cycles and then determine images that correspond to a specified phase of the motion cycle data are known as retrospective gating techniques.

In these gating methods organ motion can be detected by placing one or more sensors on the body surface and then, using the acquired information for reducing motion artifacts in the reconstructed images. Various electrical sensors and non-electrical sensors (e.g., optical, displacement, force, pressure, acceleration, microwave, and ultrasonic) can be used to detect the organ motion. The knowledge of location of these sensors can also be used for gating purposes. The motion information determined by this process can be applied for prospective or retrospective techniques. With mechanical sensors, additional external activity can be obtained. As an example, an imaging technician can visualize mechanical traces that indicate if the patient is actually stationary after being instructed to hold breadth and use the information to start and stop image acquisition. Both electrical and non-electrical sensors can vary in size from micrometers to centimeters in diameter and height. The size and number of sensors selected is usually based on the physical, physiological, and imaging requirements of the application.

Some examples of these gating applications and sensor types are:

A. ECG Gating:

Electrocardiogram (ECG) triggering techniques are techniques in which image acquisition is triggered by a start pulse derived from an ECG taken from the patient while imaging. ECG gating techniques are useful whenever data acquisition is too slow to occur during a short fraction of the cardiac cycle. Image blurring due to cardiac-induced motion occurs for imaging times of above approximately 50 ms in systole, while for imaging during diastole the critical time is of the order of 200 to 300 ms. The electronic set-up is such that an ECG signal is fed into a circuit which produces a trigger signal, to be used as a start signal for data acquisition of the imaging system. The imaging system then automatically acquires data for a time series of images from a single or multiple positions.

B. Mechanical Gating:

Mechanical triggering techniques are techniques in which image acquisition is triggered by a start pulse derived from mechanical sensors taken from the patient while imaging. Mechanical gating techniques are useful whenever data acquisition is too slow to occur during a short fraction of the cardiac cycle. Unlike an ECG based technique, mechanical gating directly corresponds to the mechanical motion of the heart. Therefore, a mechanical gating can be robust even in cases where electrical activity of the heart may not correspond to its mechanical activity. The timing of mechanical triggering can be dependent only on the sensed mechanical motion. However, the mechanical gating can be very sensitive to the ambient motion that is independent of the organ motion. Usually, ambient motion can be compensated by using differential analysis of two matched sensors, one attached to the patient and other attached to an external structure touching the patient. The electronic set-up is such that the differential mechanical signal is fed into a circuit that produces a trigger signal, to be used as a start signal for data acquisition of the imaging system. The triggering system can be set up to produce a signal during end systole or end diastole. The imaging system then automatically acquires data for a time series of images from a single or multiple positions.

C. Respiratory Gating:

Respiratory gating involves a mechanical gating technique wherein a quiescent phase of a respiration cycle is used to gate image acquisition. It can be used when a patient cannot hold breadth for the required duration during image acquisition. The patient is instructed to use a relaxed breathing technique during the acquisition. Alternatively, respiratory gating can be used in conjunction with cardiac gating to acquire images during minimal organ motion.

Figure 4:
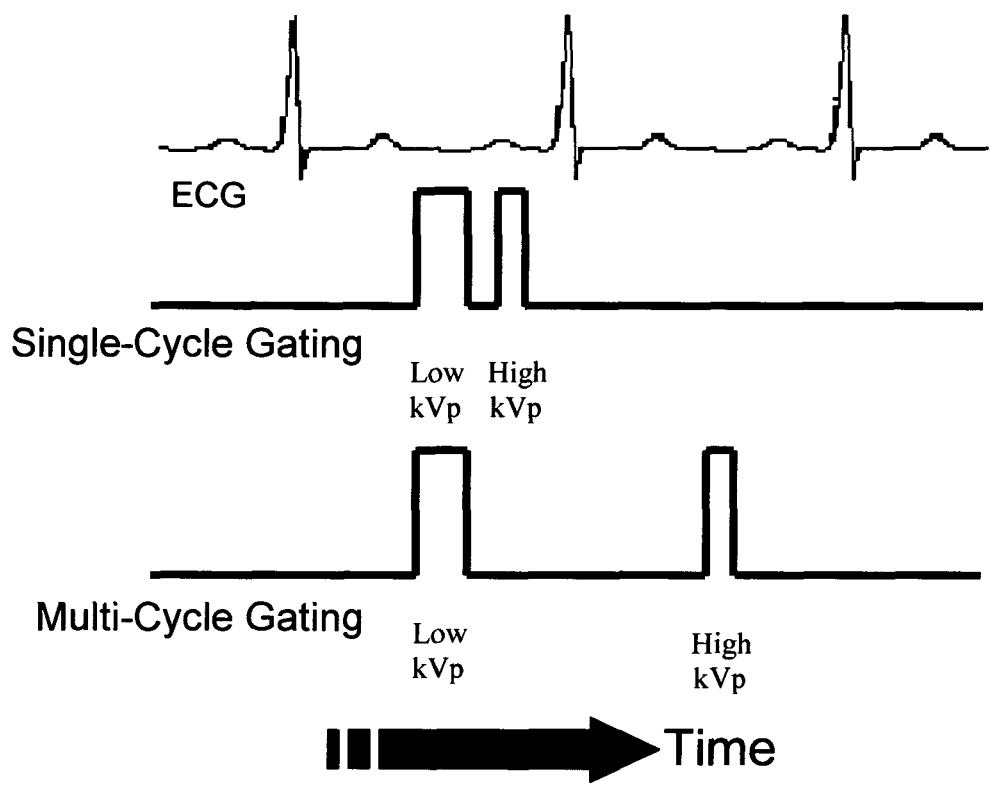
FIG. 4 is a schematic illustration of the timing of the two exposures in a gated dual-energy procedure.
Figure 5:
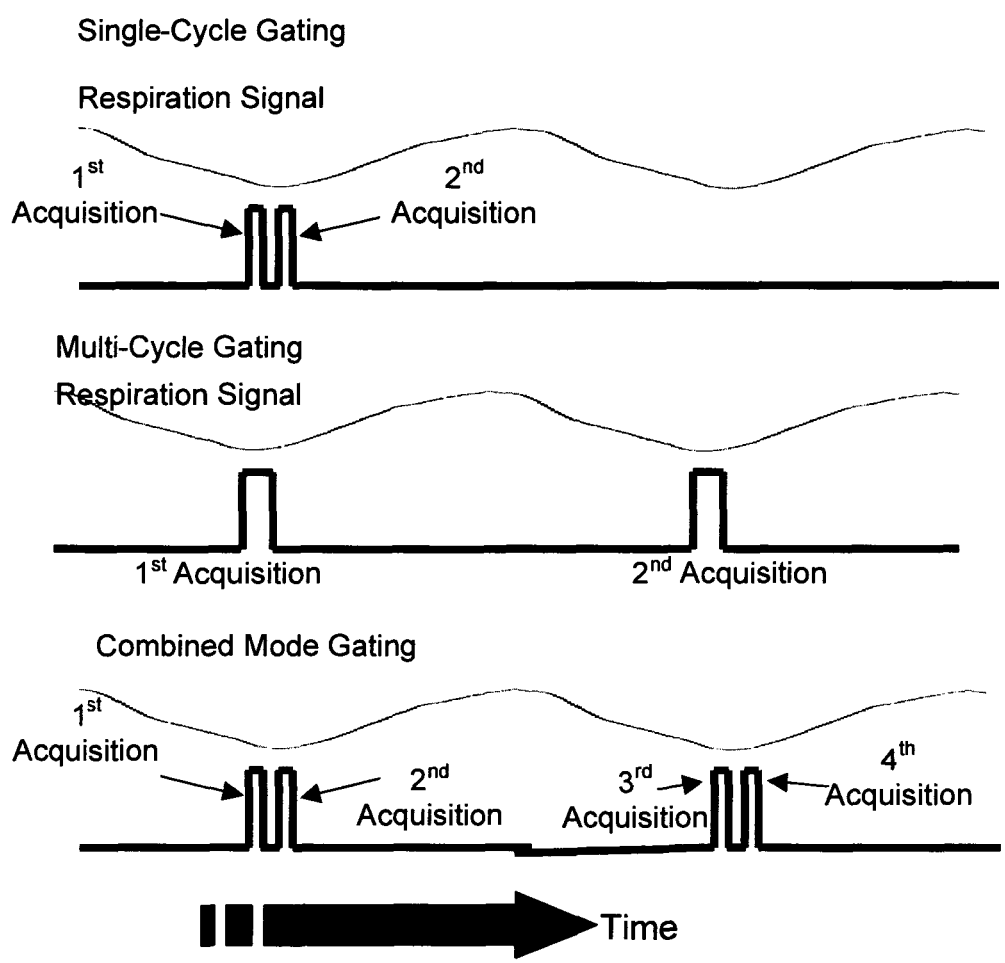
FIG. 5 illustrates Single-Cycle, Multi-Cycle, and Combined Mode gating.

Gating Modes:

Depending on the particular imaging task and anatomy/pathology of interest different gating acquisitions may be desired for optimal results. Previous work has addressed the issue of synchronizing the acquisition of the digital image with the specifics of the detector timing sequence. The herein described methods and apparatus are focused on the synchronizing of the application (including detector timing) with the clinical application. The gating modes can be divided into three general categories, Single-Cycle, Multi-Cycle, and Combined Mode (see FIGS. 4 and 5).

A) Single-Cycle:

In the Single-Cycle gating mode, the focus is on acquiring all of the exposures within a single physiological cycle (for example within a single heartbeat or respiratory cycle). One application of this would be to acquire both exposures in a dual-energy imaging pair within the same cardiac cycle, preferentially within the end diastole part of the heart cycle when the heart is relatively at rest. In this way, both exposures would occur with minimal time separation, and with minimal displacement of the heart. This would enable improved imaging of cardiac structures and pathology like cardiac calcifications compared to un-gated dual-energy acquisitions. Similarly, respiratory gating could be used to enable tomosynthesis acquisition within a single respiratory cycle for patients incapable of maintaining a breath-hold on demand (for example in pediatric patients).

B) Multi-Cycle:

In the Multi-Cycle gating mode, the focus is on acquiring all of the exposures at the same phase within a physiological cycle. An example is acquiring images at a fixed point in the R-to-R wave cycle in the ECG QRS heart cycle. One application of this would be to acquire both exposures in a dual-energy imaging pair at the same point in the heart cycle for the optimal imaging of cardiac calcifications. Similarly this would enable thoracic tomosynthesis on multiple respiratory and cardiac cycles for a patient who is either in a free-breathing situation, or unable to hold a breath for the entire imaging time. The multi-cycle gating mode could be employed on subsequent physiological cycles, or on intermittent or repeated physiological cycles.

C) Combined Mode:

The combined mode applies when the acquisition requires greater than two exposures. It refers to the repeated acquisition of multiple images in a single cycle, over multiple cycles. An example of this mode is the acquisition of an extended tomosynthesis image series. Tomosynthesis exams can require the acquisition of over 40 images; this could be done on over 40 sequential respiratory cycles, or with a few multiple images acquired during the same phase on multiple respiratory cycles (see FIG. 5). The combined mode enables acquisition that is more rapid if the physiological motion and exposure times are conducive to this approach.

Exposure Timing:

Given that multiple exposures are required for these digital radiographic applications, gating will enable some flexibility in determining the timing of the exposures. For given imaging tasks, different exposure times within a physiological cycle may be optimal. The herein described methods and apparatus enable the optimization of the acquisition time of each exposure. This optimization can be based upon the rate of the physiological cycle (for example, the heart rate) the duration of the exposures, and the gating mode. For example, the single-cycle gating mode may be used for cardiac gating only for patients with heart rates slow enough to acquire both exposures within a given cardiac phase window. The duration of the phase window would depend on the exposure time. The exposure time can be fixed by the operator, determined by a low-dose pre-exposure, or determined dynamically during the first acquisition in the series. An example sequence for dual-energy cardiac gated acquisition would be as follows:

1. Acquire low-dose exposure of patient to automatically determine the optimal acquisition parameters such as kVp's, mA's, and exposure times. For one example of Automatic Optimization of Parameters (AOP) details in a digital mammography setting see "Optimized exposure control in digital mammography", SPIE'04 by Remy Klauz et al.

2. Acquire cardiac ECG signal from multiple cardiac cycles (this can be at the same time as step 1).

3. Algorithmically determine if both exposures can be acquired within the end diastole period of the same cardiac cycle (Single-Cycle mode), or if multi-beat mode is required (long exposures, and/or rapid heart rate detected).

4. Acquire first exposure triggered at desired phase in cardiac cycle.

5. Verify decision in step 3 if desired, i.e.: if Single-Cycle was decided upon, but the heart rate changed, then revert to Multi-Cycle or vice-versa.

6. Acquire second exposure triggered at desired phase in cardiac cycle.

Another significant embodiment enabled by the herein described methods and apparatus is to alter the point in the physiological cycle when each exposure is initiated. If the goal of the gating procedure is to reduce motion, then for exposures that are all of the same duration is makes the most sense if all of the exposures are triggered to occur at the same phase in the given physiological cycle. However, if the exposures are of different durations as in the case of dual-energy imaging, motion artifact reduction may be optimal if the exposures are centered at the same point in the physiological phase requiring initiating the exposures at different phases (see FIG. 6 wherein in the lower example, the second exposure is initiated at a later phase in the cardiac cycle so that both exposures are 'centered' at the same phase in the cardiac cycle). Alternatively, some motion of the organs being imaged may be desired. In this case, the two or more image acquisitions could be triggered to occur at different phases in the physiological cycle being gated.

TABLE 1

Summary of Variables Considered

| 1. Organ Functions for Gating | 2. Gating Types | 3. Gating Modes | 4. Gating Opportunities | 5. Gating Applications With or without AOP |
|---|---|---|---|---|
| Cardiac gating | Electrical (e.g., ECG) | Single Cycle | Once/cycle | Dual/multi Energy (2 or 3 images) |
| Respiratory gating | Mechanical (e.g., MKG, respiratory) | Multi-cycle | Multiple/cycle | Tomosynthesis (10–80 images) |
| Peripheral gating (pulse-oximetry) | Combined | | | Temporal Analysis (1 or more images separated in time) |

All the variables considered for gating are summarized in Table 1. It should be understood that one or more elements in each column could be combined with one or more elements in other columns to produce a variety of possible combinations. For example, "respiratory gating" in column 1 can be combined with "electrical mode" (e.g., impedance plethysmography) in column 2 to produce single cycle mode (column 3) with multiple acquisitions/cycle (column 4) for a tomosynthesis application (column 5). It is contemplated that the benefits of the invention accrue to all such possibilities.

Technical effects include improved image quality as a result of the reduction or elimination of motion artifacts. This reduction in artifacts will enable the development of many new and clinically relevant applications. Some examples of these applications are:

a) Measurement of Heart Size:

Heart size measurements can be made from standard single-exposure chest x-ray as well as soft-tissue dual-energy images. It is desirable to be able to make accurate measurements repeatable, or to have accurate measurements for follow-up exams of the same patient. Knowing the pixel size of the image and the magnification factor of the image (based on source to image distance, digital detector to patient barrier distance), the length measurements can be made on the image. These measurements can be used to assess if the heart is enlarged. For repeatable measurements, cardiac and respiratory gating is useful to remove any discrepancies, since normal contraction and expansion of the heart and thoracic cavity during the respiratory and cardiac cycles could obscure pathological changes in size.

b) Cardiac Calcification Visualization/Measurement:

Cardiac calcifications are not always visualized on single exposures of the chest. The bone image of a dual energy image pair can better display the calcifications as shown in FIG. 7. In order to reliably display and allow more accurate qualitative and quantitative measurements, cardiac gating is useful.

c) Long Nodule Measurement:

Measurement of lung nodule size and volume from high-resolution CT exams is becoming increasingly common in lung cancer management. Although it is not possible to determine nodule volume from chest x-rays, nodule volume measurements may be possible on tomosynthesis images. However, respiratory and cardiac motion would prevent accurate estimates of nodule volume. With gated acquisition, lung nodule characterization can be performed from tomosynthesis images. With gating, nodule characterization may even be possible with single, dual-energy soft tissue images. Cardiac and respiratory gating is useful for repeatable shape and size measurements.

d) Consistent and Improved Visualization of Pulmonary Structures

Current chest x-ray techniques involve imaging of the lung at arbitrary points in the cardiac cycle. With cardiac gating, the bronchial structure could be imaged at a consistent point in the cardiac cycle, or images acquired at different points in the cardiac cycle could be compared. This may enable improved diagnosis of cardio-pulmonary pathology including diseases such as pulmonary hypertension. There is also debate among radiologists concerning the optimal point in the cardiac cycle to obtain the best visualization of lung structures.

Exemplary embodiments are described above in detail. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:

1. A method for gating multiple acquisitions, said method comprising:
    determining at least one gating signal based on a physiological signal from a subject being imaged by an imaging system, the physiological signal comprising a temporal length of each of a plurality of cardiac cycles of a subject;
    determining, based upon an average cardiac cycle temporal length of the plurality of cardiac cycles and upon knowledge of the imaging system's capabilities, a timing of each of a plurality of exposures within multiple cardiac cycles; and
    based on the determined timing of each of the plurality of exposures, initiating two exposures during the multiple cardiac cycles of the subject so as to perform the multiple acquisitions, with each of the two exposures being initiated so as to align a center point of the respective exposure with a common point of a same physiological phase in the multiple cardiac cycles; and
    wherein the two exposures comprise dual-energy exposures.

2. A system comprising:
    an x-ray source;
    an x-ray detector positioned to receive x-rays emitted from the x-ray source; and
    a computer programmed to:
        detect a first temporal length of a first cardiac cycle of a subject;
        detect a second temporal length of a second cardiac cycle of the subject;
        determine an average cardiac cycle temporal length of a plurality of cardiac cycles of the subject, the plurality of cardiac cycles comprising the first and second cardiac cycles;
        determine a number of x-ray exposures to be acquired in a single cardiac cycle of the subject based on the average cardiac cycle temporal length;
        initiate two x-ray exposures during one or more cardiac cycles of the subject based on the number of x-ray exposures to be acquired in a single cardiac cycle of the subject, the two x-ray exposures comprising dual-energy exposures;
        acquire x-ray data for each of the two x-ray exposures; and
        construct an image based on the acquired x-ray data;
    wherein, in determining the number of x-ray exposures and initiating the two x-ray exposures, the computer is further programmed to:
        initiate the two x-ray exposures in a single cardiac cycle if it is determined that the two x-ray exposures can occur within the average cardiac cycle temporal length; and
        initiate the two x-ray exposures in consecutive cardiac cycles of the subject if it is determined to initiate only a single x-ray exposure in a single cardiac cycle of the subject, with each of the two x-ray exposures being initiated so as to align a center point of the respective exposure with a common point of a same physiological phase in the consecutive cardiac cycles.

3. The system of claim 2 wherein the computer is further programmed to:
    determine if the subject is moving; and
    delay the initiation of at least one x-ray exposure of the two x-ray exposures if it is determined that the subject is moving.

4. The system of claim 2 wherein the computer is further programmed to determine a stability of a heart rhythm of the subject based on the first and second temporal lengths, and wherein the computer, in being programmed to initiate the two x-ray exposures, is programmed to initiate the two x-ray exposures based on the number of x-ray exposures and based on the stability.

5. The system of claim 2 wherein the computer, in being programmed to initiate the two x-ray exposures, is programmed to initiate the two x-ray exposures within a diastolic phase of the one or more cardiac cycles of the subject.

6. The system of claim 2 wherein the two x-ray exposures comprise a dual-energy image sequence.

7. The system of claim 2 wherein the two x-ray exposures comprise a tomosynthesis image sequence.

8. The system of claim 2 wherein the computer is further programmed to:
    combine gating parameter data that is associated with the initiation of the two x-ray exposures with the x-ray data; and
    display the constructed image, wherein the constructed image depicts the gating parameter data and the x-ray data.

9. A non-transitory computer readable medium having stored thereon a computer program comprising instructions which when executed by a computer cause the computer to:
    determine an average cardiac cycle length of a plurality of cardiac cycle lengths;
    determine a temporal length of a first prospective x-ray exposure;

determine a temporal length of a second prospective x-ray exposure;

determine whether the first and second prospective x-ray exposures can occur within the average cardiac cycle length based on the temporal lengths of the first and second prospective x-ray exposures;

initiate the first and second prospective x-ray exposures in a single cardiac cycle if the determination determines that the first and second prospective x-ray exposures can occur within the average cardiac cycle length;

initiate the first and second prospective x-ray exposures in respective subsequent cardiac cycles if the determination determines that the first and second prospective x-ray exposures cannot occur within the average cardiac cycle length; and construct an image based on at least one of the initiated first prospective x-ray exposure and the initiated second prospective x-ray exposure;

wherein the first and second prospective x-ray exposures comprise a dual-energy exposure; and wherein the first and second prospective x-ray exposures are initiated so as to center the first and second prospective x-ray exposures at a same point in a physiological phase in the respective subsequent cardiac cycles if the determination determines that the first and second prospective x-ray exposures cannot occur within the average cardiac cycle length.

10. The non-transitory computer readable storage medium of claim 9 having further instructions to cause the computer to trigger the initiation of the first and second prospective x-ray exposures based on a respiratory and cardiac gating scheme.

11. The non-transitory computer readable storage medium of claim 9 wherein the initiated first and second prospective x-ray exposures occur in a diastolic phase of one of the single cardiac cycle and the respective subsequent cardiac cycles.

12. The non-transitory computer readable storage medium of claim 9 having further instructions to cause the computer to:
determine a stability of a heart rate of a subject; and
delay initiation of the second prospective x-ray exposure based on the stability of the heart rate.

13. The non-transitory computer readable storage medium of claim 9 having further instructions to cause the computer to:
determine if a subject is moving; and
delay initiation of the second prospective x-ray exposure if the determination determines that the subject is moving.

14. The non-transitory computer readable storage medium of claim 9 wherein the image depicts a region in a subject and information representative of a gating scheme.

15. The non-transitory computer readable storage medium of claim 9 wherein the initiated first prospective x-ray exposure is at a first energy and the initiated second prospective x-ray exposure is at a second energy different than the first energy.

16. The non-transitory computer readable storage medium of claim 9 wherein the temporal length of the first prospective x-ray exposure is different than the temporal length of the second prospective x-ray exposure.

17. The non-transitory computer readable storage medium of claim 16 wherein the temporal length of the first prospective x-ray exposure is centered about a first point in a first cardiac cycle and the temporal length of the second prospective x-ray exposure is centered about a second point in a second cardiac cycle, and wherein the first point in the first cardiac cycle and the second point in the second cardiac cycle correspond to the same point in a physiological phase.

18. A method for x-ray imaging comprising:
determining whether a first x-ray exposure and a second x-ray exposure can be implemented within one cardiac cycle of a subject based on an average cardiac cycle length of the subject;
determining a gating scheme to trigger the first and second x-ray exposures based on the determination of whether the first x-ray exposure and the second x-ray exposure can be implemented within one cardiac cycle of the subject;
generating the first x-ray exposure via an x-ray source at a first time determined by the gating scheme;
generating the second x-ray exposure via the x-ray source at a second time determined by the gating scheme;
constructing an image based on at least one of the first x-ray exposure and the second x-ray exposure; and
displaying the image to a user;
wherein the first and second x-ray exposures are dual-energy exposures; and
wherein the first x-ray exposure has a first temporal length and the second x-ray exposure has a second temporal length that is different than the first temporal length, with the first x-ray exposure and the second x-ray exposure being triggered so as to center each of the first x-ray exposure and the second x-ray exposure about a same point in a physiological phase in different cardiac cycles.

19. The method of claim 18 further comprising:
determining a heart rate of the subject prior to generating the first x-ray exposure;
determining if the heart rate has changed after generating the first x-ray exposure; and
modifying the gating scheme prior to generating the second x-ray exposure if the heart rate has changed.

20. The method of claim 18 further comprising:
sensing if the subject is moving via a motion sensing device;
wherein generating the first x-ray exposure comprises generating the first x-ray exposure if the subject is not moving; and
wherein generating the second x-ray exposure comprises generating the second x-ray exposure if the subject is not moving.

21. The method of claim 18 wherein the first time corresponds to a diastolic phase of a first cardiac cycle of the subject and the second time corresponds to a diastolic phase of a second cardiac cycle different than the first cycle.

22. The method of claim 18 wherein the first and second times correspond to a diastolic phase of one cardiac cycle.

23. The method of claim 18 wherein the gating scheme is further based on an exposure length of the first x-ray exposure and an exposure length of the second x-ray exposure.

24. The method of claim 18 wherein the image depicts a region of a subject and gating information.

25. The method of claim 18 wherein the first and second x-ray exposures comprise one of a tomosynthesis image sequence and a dual-energy image sequence.

* * * * *